(12) United States Patent
Groux et al.

(10) Patent No.: US 7,985,409 B2
(45) Date of Patent: Jul. 26, 2011

(54) TR1 CELLS FOR USE IN ATHEROSCLEROSIS

(75) Inventors: Hervé Groux, Le Rouret (FR); Alain Tedgui, Paris (FR); Ziad Mallat, Herbeville (FR); Valérie Brun, Biot (FR)

(73) Assignees: INSERM (Institut National de la Sante et de la Recherche Medicale), Paris (FR); TxCell, Valbonne (FR)

( * ) Notice: Subject to any disclaimer, the term of this patent is extended or adjusted under 35 U.S.C. 154(b) by 506 days.

(21) Appl. No.: 11/660,113

(22) PCT Filed: Aug. 11, 2004

(86) PCT No.: PCT/IB2004/002858
§ 371 (c)(1),
(2), (4) Date: Sep. 5, 2007

(87) PCT Pub. No.: WO2006/018674
PCT Pub. Date: Feb. 23, 2006

(65) Prior Publication Data
US 2008/0107663 A1    May 8, 2008

(51) Int. Cl.
A61K 35/16    (2006.01)
(52) U.S. Cl. .................... 424/93.71; 424/93.21
(58) Field of Classification Search .......... None
See application file for complete search history.

(56) References Cited

U.S. PATENT DOCUMENTS

| 7,771,932 B1 * | 8/2010 | Groux et al. ............ 435/6 |
| 2002/0034500 A1 | 3/2002 | Levings et al. |
| 2004/0191235 A1 * | 9/2004 | Groux et al. ............ 424/93.71 |

FOREIGN PATENT DOCUMENTS

| WO | WO 02/092793 A1 | 11/2002 |
| WO | WO 2005000344 A2 * | 1/2005 |

OTHER PUBLICATIONS

Groux #2 et al., Transplantation. May 15, 2003;75(9 Suppl):8S-12S.*
Mallat, Z., et al., "Induction of a Regulatory T Cell Type 1 Response Reduces the Development of Atherosclerosis in Apolipoprotein E-Knockout Mice," Circulation, 2003, pp. 1232-1237, vol. 108(10).
Groux, H., et al., "A CD4+ T-Cell Subset Inhibits Antigen-Specific T-Cell Responses and Prevents Colitis," Nature, 1997, pp. 737-742, vol. 389(6652), MacMillan Journals, Ltd., London, United Kingdom.
Wakkach, A., et al., "Characterization of Dendritic Cells that Induce Tolerance and T Regulatory 1 Cell Differentiation In Vivo," Immunity, 2003, pp. 605-617, vol. 18(5), Cell Press, USA.
McGuirk, P., et al., "Pathogen-Specific T Regulatory 1 Cells Induced in the Respiratory Tract by a Bacterial Molecule that Stimulates Interleukin 10 Production by Dendritic Cells: A Novel Strategy for Evasion of Protective T Helper Type 1 Responses by Bordetella pertussis," Journal of Experimental Medicine, 2002, pp. 221-231, vol. 195(2), Tokyo, Japan.

International Search Report for PCT/IB2004/002858 completed Nov. 2, 2004.
Barrat, F., et al., "In Vitro Generation of Interleukin 10-Producting Regulatory CD4+ T Cells is Induced by Immunosuppressive Drugs and Inhibited by T Helper-Type 1 (Th1) and Th2-Inducing Cytokines", J. Exp. Med., Mar. 4, 2002, vol. 195, No. 5, pp. 603-616.
Binder, C., et al., "Pneumococcal Vaccination Decreases Atherosclerotic Lesion Formation: Molecular Mimicry Between Streptococcus pneumoniae and Oxidized LDL", Nature Medicine, Jun. 2003, vol. 9, No. 6, pp. 736-743.
Cavani, A., et al., "Human CD4+ T Lymphocytes with Remarkable Regulatory Functions on Dendritic Cells and Nickel-Specific Th1 Immune Responses", The Journal of Investigative Dermatology, 2000, vol. 114, pp. 295-302.
Chen, Y., et al., "Regulatory T Cell Clones Induced by Oral Tolerance: Suppression of Autoimmune Encephalomyelitis", Science, Aug. 1994, vol. 265, pp. 1237-1240.
Cottrez, F., et al., "T Regulatory Cells 1 Inhibit a Th2-Specific Response In Vivo", The Journal of Immunology, 2000, vol. 165, pp. 4848-4853.
Daugherty, A., et al., "T Lymphocytes in Atheroscleropsis: The Yin-Yang of Th1 and Th2 Influence on Lesion Formation", Circulation Research, 2002, vol. 90, pp. 1039-1040.
Doetze, A., et al., "Antigen-Specific Cellular Hyporesponsiveness in a Chronic Human Helminth Infection is Mediated by $T_h3/T_r1$-Type Cytokines IL-10 and Transforming Growth Factor-β but not by a $T_h1$ to $T_h2$ Shift", International Immunology, 2000, vol. 12, No. 5, pp. 623-630.
Fukaura, H., et al., "Induction of Circulating Myelin Basic Protein and Proteolipid Protein-Specific Transforming Growth Factor-b1-Secreting Th3 T Cells by Oral Administration of Myelin in Multiple Sclerosis Patients", J. Clin. Invest., Jul. 1996, vol. 98, No. 1, pp. 70-77.
Glass, C., et al., "Atherosclerosis: The Road Ahead", Cell, Feb. 2001, vol. 104, pp. 503-516.
Groux, H., "An Overview of Regulatory T Cells", Microbes Infect., 2001, vol. 3, pp. 883-889.
Gupta, S., et al., "IFN-γ Potentiates Atherosclerosis in ApoE Knock-Out Mice", J. Clin. Invest., Jun. 1997, vol. 99, No. 11, pp. 2752-2761.
Hansen, P., et al., "Freunds Adjuvant Alone is Antiatherogenic in apoE-deficient Mice and Specific Immunization Against TNFα Confers no Additional Benefit", Atherosclerosis, 2001, vol. 158, pp. 87-94.
Hansson, G., "Immune Mechanisms in Atherosclerosis", Arterioscler. Thromb. Vasc. Biol., 2001, vol. 21, pp. 1876-1890.
Laurat, E., et al., "In Vivo Downregulation of T Helper Cell 1 Immune Responses Reduces Atherogenesis in Apolipoprotein E-Knockout Mice", Circulation, 2001, vol. 104, pp. 197-202.
Lee, T-S., et al., "The Role of Interleukin 12 in the Development of Atherosclerosis in ApoE-Deficient Mice", Arterioscler. Thromb. Vasc. Biol., 1999, vol. 19, pp. 734-742.

(Continued)

Primary Examiner — Zachary Skelding
(74) Attorney, Agent, or Firm — Young & Thompson (57) ABSTRACT

The present invention relates to a method of treating or preventing atherosclerosis comprising administering to a mammal in need of such a treatment a) an antigen which has been used to activate in vitro a Tri cell population originating from said mammal, and b) the TO cell population activated by said antigen, said TO cell population being obtained from a CD4+ T lymphocyte population of said mammal.

17 Claims, 2 Drawing Sheets

OTHER PUBLICATIONS

Levings, M.K., et al., "IFN-a and IL-10 Induce the Differentiation of Human Type 1 T Regulatory Cells", *The Journal of Immunology*, 2001, vol. 166, pp. 5530-5539.

Liuzzo, G., et al., "Molecular Fingerprint of Interferon-y Signaling in Unstable Angina", *Circulation*, Mar. 2001, vol. 103, pp. 1509-1514.

Liuzzo, G., et al., "Monoclonal T-Cell Proliferation and Plaque Instability in Acute Coronary Syndromes", *Circulation*, 2000, vol. 101, pp. 2883-2888.

Liuzzo, G., et al., "Perturbation of the T-Cell Repertoire in Patients with Unstable Angina", *Circulation*, Nov. 1999, vol. 100, pp. 2135-2139.

Lusis, A., "Atherosclerosis", *Nature*, Sep. 2000, vol. 407, pp. 233-241.

MacDonald, A.J., et al., "CD4 T Helper Type 1 and Regulatory T Cells Induced Against the Same Epitopes on the Core Protein in Hepatitis C Virus—Infected Persons", *The Journal of Infectious Diseases*, 2002, vol. 185, pp. 720-727.

Mallat, Z., et al., "Increased Plasma Concentrations of Interleukin-18 in Acute Coronary Syndromes", *Heart*, 2002, vol. 88, pp. 467-469.

Mallat, Z., et al., "Protective Role of Interleukin-10 in Atherosclerosis", *Circ. Res.*, 1999, vol. 85, pp. 17-24.

Mallat, Z., et at, "Interleukin-18/Interleukin-18 Binding Protein Signaling Modulates Atherosclerotic Lesion Development and Stability", *Circ. Res.*, 2001, vol. 89, pp. 41-45.

McGuirk, P. et al., "Pathogen-Specific Regulatory T Cells Provoke a Shift in the Th1/Th2 Paradigm in Immunity to Infectious Diseases", *Trends in Immunology*, Sep. 2002, vol. 23, No. 9, pp. 450-455.

Oslund, L.J., et al., "Interleukin-10 Blocks Atherosclerotic Events In Vitro and In Vivo", *Arterioscler. Thromb. Vasc. Biol.*, 1999, vol. 19, pp. 2847-2853.

Pinderski, L.J., et al., "Overexpression of Interleukin-10 by Activated T Lymphocytes Inhibits Atherosclerosis in LDL Receptor-Deficient Mice by Altering Lymphocyte and Macrophage Phenotypes", *Circ. Res.*, 2002, vol. 90, pp. 1064-1071.

Roncarolo, M.G., et al., "Type 1 Regulatory Cells", *Immunological Reviews*, 2001, vol. 182, pp. 68-79.

Shevach, E.M., "Regulatory T Cells in Autoimmunity", *Annu. Rev. Immunol.*, 2000, vol. 18, pp. 423-449.

Von Der Thusen, J.H., et al., "Attenuation of Atherogenesis by Systemic and Local Adenovirus-Mediated Gene Transfer of Interleukin-10 in LDLr$^{-/-}$ Mice", *The FASEB Journal*, Dec. 2001, vol. 15, pp. 2730-2732.

Whitman, S.C., et al., "Interleukin-18 Enhances Atherosclerosis in Apolipoprotein E$^{-/-}$ Mice Through Release of Interferon-γ", *Circulation Research*, 2002, vol. 90, pp. e34-e38.

Whitman, S.C., et al., "Exogenous Interferon-γ Enhances Atherosclerosis in Apolipoprotein E$^{-/-}$ Mice", *American Journal of Pathology*, Dec. 2000, vol. 157, No. 6, pp. 1819-1824.

Zhou, X., et al., "Transfer of CD4+ T Cells Aggravates Atherosclerosis in Immunodeficient Apolipoprotein E Knockout Mice", *Circulation*, 2000, vol. 102, pp. 2919-2922.

* cited by examiner

TR1 CELLS FOR USE IN ATHEROSCLEROSIS

The present invention relates to a method of treating or preventing atherosclerosis comprising administering to a mammal in need of such a treatment:
a) an antigen which has been used to activate in vitro a Tr1 cell population originating from said mammal, and
b) the Tr1 cell population activated by said antigen, said Tr1 cell population being obtained from a CD4+ T lymphocyte population of said mammal.

BACKGROUND OF INVENTION

Atherosclerosis is a cardiovascular condition occurring as a result of narrowing down of the arterial walls. The narrowing is due to the formation of plaques (raised patches) or streaks in the inner lining of the arteries. These plaques consist of foam cells of low-density lipoproteins, oxidized-LDL, decaying muscle cells, fibrous tissue, clumps of blood platelets, cholesterol, and sometimes calcium. They tend to form in regions of turbulent blood flow and are found most often in people with high concentrations of cholesterol in the bloodstream. The number and thickness of plaques increase with age, causing loss of the smooth lining of the blood vessels and encouraging the formation of thrombi (blood clots). Sometimes fragments of thrombi break off and form emboli, which travel through the bloodstream and block smaller vessels.

The blood supply is restricted to the heart, eventually forming a blood clot leading to death. The major causes of atherosclerosis are hypercholesterolemia and hyperlipidemia is high circulating cholesterol and high lipids like LDL-cholesterol and triglycerides in the blood. These lipids are deposited in the arterial walls, obstructing the blood flow and forming atherosclerotic plaques leading to death.

Atherosclerosis is responsible for more deaths in countries, such as in the Unites States of America, than any other single condition. Atherosclerotic heart disease involving the coronary arteries is the most common single cause of death, accounting for one third of all deaths. Atherosclerotic interference with blood supply to the brain (causing stroke) is the third most common cause of death after cancer. Atherosclerosis also causes a great deal of serious illness by reducing the blood flow in other major arteries, such as those to the kidneys, the legs and the intestines.

Medication is not a satisfactory treatment because much of the damage to the artery walls has already been done. Anticoagulant drugs have been used to try to minimize secondary clotting and embolus formation, but have little or no effect on the progress of the disease. Vasodilator drugs are used to provide symptom relief, but are of no curative value.

Surgical treatment is available for certain high-risk situations. Balloon angioplasty can open up narrowed vessels and promote an unproved blood supply. The blood supply to the heart muscle can also be restored through a vein graft bypass. Large atheromatous and calcified arterial obstructions can be removed by endarterectomy, and entire segments of diseased peripheral vessels can be replaced by woven plastic tube grafts.

There is a need for a new therapy, possibly to prevent these conditions and insure better health, particularly in people who are genetically predisposed to such conditions. The present invention fulfills these and other needs.

There is now accumulating evidence for a novel functionally distinct subpopulation of T cells, called regulatory T cells that exert important regulatory functions in various immuno-inflammatory diseases (see references 12 to 14 for review). Several subsets of regulatory T (Tr) cells with distinct phenotypes and distinct mechanisms of action have now been identified. These include Tr1 cells (15 to 20), which secrete high levels of interleukin (IL)-10 and low to moderate levels of transforming growth factor (TGF)-$\beta$, Th3 cells (21,22), which primarily secrete TGF-$\beta$, and CD4+CD25+ T cells, which inhibit immune responses through cell-cell contact (23). We have shown that repeated stimulation of naive T cells, from OVA T-cell receptor (TCR)-transgenic mice with OVA and IL-10, results in the generation of T-cell clones with a unique cytokine profile distinct from that of Th0, Th1 or Th2 cells (15). These Tr1 cells produce IL-10, IL-5 and IFN-$\gamma$, with or without TGF-$\beta$, but with little or no IL-2 or IL-4, and proliferate poorly following polyclonal TCR-mediated activation. Functional studies have shown that Tr1 cells have immunosuppressive properties and have been shown to prevent the development of Th1-mediated autoimmune diseases (15). Co-culture of naïve CD4+ T cells and human Tr1 clones in the presence of allogenic antigen-presenting cells (APCs) results in the suppression of proliferative responses (15). Similarly, Tr1 clones specific for filamentous haemaggultinin (HA) from *Bordetella pertussis* suppress proliferation and cytokine production by a Th1 clone against an unrelated antigen, influenza virus HA (20). In both cases, the suppressive effects of Tr1-cell clones are reversed by neutralizing IL-10, suggesting that, regardless of their antigen specificities, Tr1 cell suppression is a bystander effect mediated through the production of IL-10.

Here, we tested whether transfer of Tr1 cells in mammals could reduce immune inflammatory processes and more specifically could reduce risk of artherosclerosis. We show for the first time that transfer of such Tr1 cells to apoE knockout (KO) mice inhibits pathogenic Th responses and reduces the development of atherosclerosis.

DESCRIPTION OF THE INVENTION

A first subject of the present invention is a method of treating or preventing atherosclerosis comprising administering sequentially, simultaneously or separately to a mammal in need of such a treatment:
a) an antigen which has been used to activate in vitro a Tr1 cell population originating from said mammal, and
b) the Tr1 cell population activated by said antigen, said Tr1 cell population being obtained from a CD4+ T lymphocyte population of said mammal.

The antigen administered in the method of the present invention is an immunogenic peptide. Immunogenic peptide will be referred herein as non-pathogenic peptides or proteins that can bind to MHCII molecule of an individual and that is recognized by the T cell receptor of said individual. For example, the antigen is a non-allergic food antigen or a non-pathogenic bacterial antigen. Between 0.05 mg/kg to 5 mg/kg, for example 1, 2, 3, 4 mg/kg of the antigen is administered to the mammal in need of treatment. The antigen can be administered once or twice the first month (for example at day 1 and at day 15) and then once a month for about 2 to 3 months. Routes of administration include but are not limited to intravenous, intramuscular, intra-arterial, intramedullary, intrathecal, intraventricular, transdermal, subcutaneous, preferably intravenous.

In another embodiment, the method includes administering from $10^6$ to $10^9$ antigen-activated Tr1 cells/kg, for example from 0.5 $10^7$ to 1.5 $10^7$ cells/kg, preferably $10^7$ cells/kg.

In the method as depicted above, the antigen-activated Tr1 cell population of step b) is obtainable by an in vitro preparation process comprising the following steps:

i) obtaining a Tr1 cell population from the CD4+ T lymphocyte population of the mammal in need of the treatment;
ii) in vitro activating said Tr1 cell population by contacting with an antigen; and
iii) recovering the antigen-activated Tr1 cell population.

In a preferred embodiment, step i), which is obtaining the Tr1 cell population, comprises the following steps:
a) isolating a progenitor cell population from said mammal;
b) obtaining a population of dendritic cells by culturing said progenitor cell population in presence of interleukine-10 (IL-10);
c) contacting cells of step b) with the CD4+ T lymphocyte population isolated from said mammal to allow differenciation of said CD4+ T lymphocytes into the Tr1 cell population; and
d) recovering the Tr1 cell population from the step c).

In step b), IL-10 is from 50 to 250 Uml$^{-1}$, preferably at 100 Uml$^{-1}$ in the culture medium.

The obtention of the Tr1 cell population with steps comprising contacting dendritic cells with a CD4+ T lymphocyte population, and obtening the population of dendritic cells by culturing said progenitor cell population in presence of interleukine-10 (IL-10), are described in the paragraphs "Results" and "Experimental procedures" of the publication Wakkach et al. (Immunity. 2003 May; 18(5):605-17), incorporated herein by reference.

In yet another preferred embodiment, step i) which is obtaining the Tr1 cell population comprises the following steps:
a) culturing the CD4+ T lymphocyte population in a media with an appropriate amount of alpha-interferon ($\alpha$-IFN), and
b) recovering the Tr1 cell population.

$\alpha$-IFN is preferably at 5 ng/ml in the media.

In the step a), the media may farther comprise an appropriate amount of IL-10, which is preferably at 100 Uml-1.

In step b), the Tr1 cell population is cultured in a media comprising interleukine 15 (IL-15) to allow proliferation. IL-15 is preferably at 5 ng/ml in the media.

The process of obtaining a Tr1 cell population by contacting a CD4+ T lymphocyte population with an appropriate amount of alpha-interferon ($\alpha$-IFN) is described in the paragraph "Tr1 cell differentiation" of the american patent application US 2002/0034500, which was published on Mar. 21, 2002 (LEVINGS et al) (see from p. 2, col. 2, L. 33 to p. 6, col. 1, L. 22 and claims, which are incorporated herein by reference).

In still another embodiment, the invention is directed to a method as defined above wherein the antigen-activated Tr1 cell population of step b) is obtained by an in vitro preparation process comprising the following steps:
i) in vitro activating the CD4+ T lymphocyte population in presence of the antigen, presented by artificial antigen presenting cells; and
ii) recovering an activated CD4+ T lymphocyte population comprising at least 10% of antigen-activated Tr1 cells.

Preferably, the artificial antigen presenting cells express a HLA II system molecule and a human LFA-3 molecule, and don't express the co-stimulation molecules B7-1, B7-2, B7-H1, CD40, CD23 and ICAM-1.

The preparation process of obtaining the antigen-activated Tr1 cell population wherein artificial antigen presenting cells are used is described in the international patent application WO 02/092793 published on Nov. 21, 2002, from page 5, L. 8 to 14, L. 25, which passage is incorporated herein by reference. The FIG. 1 of this patent application is also incorporated herein by reference.

In still another embodiment, the invention is directed to a method as defined above wherein the antigen-activated Tr1 cell population of step b) is obtained by an in vitro preparation process comprising the following steps:
i) in vitro activating the CD4+ T lymphocyte population in presence of an antigen and an appropriate amount of interleukine-10 (IL-10); and
ii) recovering the antigen-activated Tr1 cell population.

Preferably, IL-10 is present in the culture media at a 100 Uml$^{-1}$.

The preparation process of obtaining the antigen-activated Tr1 cell population wherein IL-10 is used is described in the scientific publication Groux et al (Nature. 1997 Oct. 16; 389 (6652):737-42) in the paragraph "Methods", which is incorporated herein by reference.

The method as described above is particularly useful for preventing, delaying the onset and/or treating humans.

A second aspect of the present invention is aimed at a product comprising:
a) an antigen which has been used to activate in vitro a Tr1 cell population originating from a mammal, and
b) the Tr1 cell population activated by said antigen, said Tr1 cell population being obtained from a CD4+ T lymphocyte population of said mammal,
as a combined preparation for simultaneous, separate or sequential use for treating or preventing atherosclerosis.

Preferably, the combined preparation is for treating or preventing atherosclerosis in said mammal.

More preferably, said product is a combined preparation for simultaneous, separate or sequential use for treating or preventing atherosclerosis in humans.

The antigen in the product may be at a dose ranging from 0.05 mg/kg to 5 mg/kg, for example 1, 2, 3, 4 mg/kg.

In one particular embodiment, the product is suitable for administration once or twice the first month (for example at day 1 and at day 15) and then once a month for about 2 to 3 months. It can be formulated for different routes of administration including intravenous, intramuscular, intra-arterial, intramedullary, intrathecal, intraventricular, transdermal, subcutaneous, preferably intravenous.

The product of the invention also comprises from $10^6$ to $10^9$ antigen-activated Tr1 cells/kg, for example from $0.5\ 10^7$ to $1.5\ 10^7$ cells/kg, preferably $10^7$ cells/kg.

In the product of the invention, the antigen-activated Tr1 cell of step b) population is obtainable by an in vitro preparation process comprising the following steps:
i) obtaining a Tr1 cell population from the CD4+ T lymphocyte population of the mammal in need of treatment;
ii) in vitro activating the Tr1 cell population by contacting it with the antigen; and
iii) recovering the antigen-activated Tr1 cell population.

In another embodiment, the product comprises Tr1 cells obtainable by a process comprising the following steps:
a) isolating a progenitor cell population from said mammal;
b) obtaining a population of dendritic cells by culturing said progenitor cell population in presence of interleukine-10 (IL-10);
c) contacting cells of step b) with the CD4+ T lymphocyte population isolated from said mammal to allow differenciation of said CD4+ T lymphocytes into the Tr1 cell population; and
d) recovering the Tr1 cell population from the step c).

The obtention of the Tr1 cell population with a step of contacting dendritic cells with a CD4+ T lymphocyte population, and the obtention of the population of dendritic cells by culturing said progenitor cell population in presence of interleukine-10 (IL-10), are described in the paragraphs "Results" and "Experimental procedures" of the scientific publication Wakkach et al. (Immunity. 2003 May; 18(5):605-17), incorporated herein by reference.

Preferably, step i) of obtaining the Tr1 cell population comprises the following steps:
a) culturing the CD4+ T lymphocyte population with an appropriate amount of alpha-interferon (α-IFN); and
b) recovering the Tr1 cell population.

Step a) may also comprises culturing in combination with an appropriate amount of IL-10. In addition, the Tr1 cell population may be further expanded with interleukine 15 (IL-15).

In the product of the invention, the antigen-activated Tr1 cell population of step b) may also be obtained by an in vitro preparation process comprising the following steps:
i) in vitro activating the CD4+ T lymphocyte population in presence of the antigen, presented by artificial antigen presenting cells; and
ii) recovering an activated CD4+ T lymphocyte population comprising at least 10% of the antigen-activated Tr1 cell population.

Preferably, the artificial antigen presenting cells express a HLA II system molecule and a human LFA-3 molecule, and don't express the co-stimulation molecules B7-1, B7-2, B7-H1, CD40, CD23 and ICAM-1.

In the product of the present invention, the antigen-activated Tr1 cell population of step b) may also be obtained by an in vitro preparation process comprising the following steps:
i) in vitro activating the CD4+ T lymphocyte population in presence of the antigen and and appropriate amount of interleukine-10 (IL-10); and
iii) recovering the antigen-activated Tr1 cell population.

The preparation process of obtaining the antigen-activated Tr1 cell population wherein IL-10 is used is described in the scientific publication Groux et al (Nature. 1997 Oct. 16; 389 (6652):737-42) in the paragraph "Methods", which is incorporated herein by reference.

The invention is also aimed at the use of a product as defined above for the manufacture of a medicament for preventing or treating artherosclerosis.

In the method and product as depicted above, Tr1 cells are featured by the following specific combination of surface markers : CD4, CD18 et/ou CD11a, et CD49b. CD3 can also be contemplated as marker.

Therefore, in another embodiment, the invention is directed to a method and product as described above, wherein Tr1 cells are obtainable by any method using said markers. For example, Tr1 cells can be identified and/or purified by Elisa, flowcytometry, immunoaffinity chromatography with antibodies directed against said markers, for example with:
APC-conjugated anti-CD4 (RPA-T4)—Becton Dickinson
PC5-conjugated anti-CD3 (UCHT-1)—Caltag
PE-conjugated anti-CD18 (6.7)—Becton Dickinson
FITC-conjugated anti-CD49b (AK-7)—Becton Dickinson
Purification of CD3+CD4+CD18brightCD49b+ Cells:
Enrichment of CD3+CD4+CD18brightCD49b+ cells from lymphocytes can be performed with magnetic beads in two steps:
depletion of the total population with anti-human Ig-magnetic beads of cells bound with human anti-CD8, anti-CD14, anti-CD56 and anti-CD19.
Selection of CD49b+ cells bound to an anti-CD49b human antibody with anti-human Ig-magnetic beads.

Further purification is possible with flowcytometry or beads with CD3, CD18 et CD49b antibodies.

ELISA tests may also be used to measure IL-4, IL-10, and l'IFN-alpha expression.

In this regard, claims and example 5 of PCT/FR 004/001583 is incorporated herein by reference.

EXAMPLES

Example 1

Methods 1.1 Generation, Expansion and Transfer of Ovalbumin (OVA)-Specific Tr1 Clones The mouse T-cell clones were obtained from DO11-10 BALB/c mice after in vitro differentiation as previously described (15). Naive (MEL-14$^{bright}$) CD4$^+$, KJ-1.26$^+$ cells were stimulated repeatedly with OVA peptide 323-339 every week for 3 weeks, in the presence of IL-10. T-cell clones were generated as previously described (15). Clones were expanded and analyzed for cytokine secretion after activation with APCs and OVA peptide. Selected clones were then stimulated with irradiated splenocytes and OVA peptide every 2 weeks and further expanded with IL-2 (R&D systems). T-cell clones were used at least 10 days after the last stimulation. Here we used clone A-10-9 that has been previously described and shown to prevent Th1- and Th2-mediated immune responses (15, 24).

Fifteen week-old female apoE KO C57B1/6 mice were immunized subcutaneously with either saline (n=11) or 50 µg of OVA in CFA (both from Sigma) (n=18) every 12 days for 9 weeks. The saline-treated mice were then divided into 2 groups that received at day 0, in addition to subcutaneous saline, a unique intra-peritoneal injection (200 µl) of either saline (n=5) or 10$^6$ OVA-specific Tr1 cells without OVA/CFA (n=6). The OVA/CFA-immunized group was divided into 2 other groups of mice which received at day 0 an intra-peritoneal injection (200 µl) of either saline (OVA/CFA group, n=9) or 10$^6$ OVA-specific Tr1 cells (OVA/CFA+Tr1 group, n=9).

1.2 Cytokine Assays

In brief, ELISA plates (Polylabo) were coated with the appropriate coating anti-cytokine mAbs (11B11, 2A5, TRFK4 and XGM-1 for IL-4, IL-10, IL-5 and IFN-γ respectively) in carbonate buffer and incubated at 4° C. overnight. Sandwich ELISA were performed as previously described (24). Plates were read on an ELISA reader at a wavelength of 405 nm after color development (Labsystems iEMS reader).

1.3 Analysis of OVA-Specific Serum IgE, IgG1 and IgG2a

OVA-specific Igs levels were measured using a two-step sandwich ELISA as described (24). To detect IgG1 and IgG2a we used biotinylated rat mAb (A85-1, and R19-15 for IgG1 and IgG2a respectively, Becton Dickinson) at 2 µg/ml. Standards for OVA-specific IgG1 were pooled sera from hyper-immunised BALB/c mice.

1.4 Purification and Culture of Spleen and Lymph Node Cells

T cells were purified from spleen or draining lymph nodes by negative selection using anti-CD11b (M1/70), anti-B220 and anti-NK cells (DX5) followed by depletion with a mixture of magnetic beads coated with anti-rat Ig (Dynal).

For cytokine measurements, purified T cells ($10^5$) were mixed with irradiated splenic APCs ($4 \times 10^5$) and OVA/CFA (0.25 mg/ml) ConA (2 µg/ml) in 96 well plates. Supernatants were collected at 24 h (for IL-4 measurements) and at 48 h (for IL-5, IL-10, and IFN-γ measurements) and assayed for cytokine levels by ELISA as previously described (24).

For the cell proliferation assay, purified T cells were mixed with irradiated splenic and ConA or OVA. One µCi of $^3$-thymidine (Perkin Elmer) was added for the last 12 h of cell culture.

1.5 Analysis of Atherosclerotic Plaque Size and Composition

Mice were sacrificed at 24 weeks of age. Plasma total and HDL-cholesterol were measured with a commercially available Cholesterol kit (Sigma). Morphometric and immunohistochemical studies were performed in the aortic sinus and the thoracic aorta (spanning from the brachiocephalic artery to the renal arteries and including the first 3 mm$^2$ of the brachiocephalic artery) as previously described (9).

Collagen fibers were stained with Sirius red. Immunohistochemical analysis was performed as previously described (9). The following primary antibodies were used: MOMA-2 (BioSource Int.) as a specific marker for macrophage; anti-mouse CD3-θ (Santa Cruz), anti-α-smooth muscle actin, alkaline phosphatase conjugate, clone 1A4 (Sigma), and anti-IL-10 antibody (Santa Cruz). At least four sections per animal were analyzed for each immunostaining. Morphometric analysis was performed with an automated image processor (Histolab, Microvision) as described (9).

1.6 Statistical Analysis

The effects of treatment on lesion area, plaque composition, serum Ig levels and cytokine production by spleen and lymph T cells were evaluated using ANOVA and Bonferroni/Dunn test or a Student t test. A value of P<0.05 was considered to be statistically significant.

Example 2

Results 2.1 Transfer of Tr1 Cells with Their Cognate Antigen Induces Immune Suppression As expected (Table 1), treatment with OVA in complete Freund's adjuvant resulted in elevated serum levels of OVA-specific antibodies, predominantly IgG2a, and to a much lesser extent IgE, in comparison with the saline-treated group where OVA-specific IgGs were undetectable. Treatment of mice with OVA/CFA induced a Th1-like response as revealed by the production of high levels of IFN-γ (Th1 cytokine), but low levels of IL-10 and no IL-4 (Th2 cytokines), by OVA-stimulated lymph T cells (Table 1). Injection of regulatory Tr1 cells alone did not alter the immune response (Table 1). However, administration of Tr1 cells to OVA/CFA-immunized animals significantly inhibited the secretion of OVA-specific IgG2a antibodies as previously reported in a model using Alum as an adjuvant (24). Moreover, the suppressive effect of Tr1 cells was confirmed by the marked decrease in IFN-γ production and proliferative response observed in the (OVA/CFA)+Tr1 group as compared with the OVA/CFA after in vitro recall response of T cells (P<0.001). This was associated with enhanced IL-10 production by T cells stimulated with OVA in vitro (P<0.001), suggesting that the transferred OVA-specific Tr1 cells were functionally active (Table 1). TGF-β in the supernatants was below detectable levels.

IL-10 is a cytokine with important immunosuppressive effect in vivo. Therefore, to analyze the consequence of high IL-10 secretion in mice transferred with Tr1 cells and treated with OVA/CFA, we analyzed the cytokine response of T cells after polyclonal activation with ConA. As expected, ConA-stimulation induced a Th0 type response in T cells from saline- or Tr1-treated mice and a Th1-type response in mice treated with OVA/CFA (Table 2). In contrast, in mice treated with regulatory Tr1 cells and OVA/CFA, we observed a marked decrease in IFN-γ production and an increase in IL-10 production by conA-stimulated T cells (Table 2). Interestingly, the ratio of INF-γ to IL-10 was reduced by 3 to 4-fold in (OVA/CFA)+Tr1 group compared to the other groups of mice, suggesting that the transfer of regulatory Tr1 cells followed by a systemic delivery of their specific antigen induced a bystander non specific regulatory immune response due to the chronic stimulation of Tr1 cells with OVA/CFA. However, as previously shown in other inflammatory models, the inhibitory function of Tr1 cells is local (15, 25), and chronic stimulation of Tr1 cells did not result in systemic secretion of IL-10 in the serum as <30 pg/ml of IL-10 was measured in the serum of the four different groups of mice.

2.2 Transfer of Tr1 Cells with Their Cognate Antigen Reduces Atherosclerotic Lesion Size in apoE Deficient Mice Serum total cholesterol and high density lipoprotein (HDL) levels did not differ between groups (Table 3). Atherosclerotic lesion size in the thoracic aorta did not differ between saline and Tr1 groups (Table 3). There was a modest but not statistically significant reduction in lesion size in the thoracic aorta of mice treated with OVA/CFA in comparison with saline or Tr1 group (P=0.09 and P=0.07, respectively). In contrast, there was a marked and highly significant reduction in lesion size in the (OVA/CFA)+Tr1 group in comparison with either OVA/CFA (42% reduction, P=0.008), Tr1 alone or saline (55% reduction, P≦0.001) (Table 3).

Figure 1:
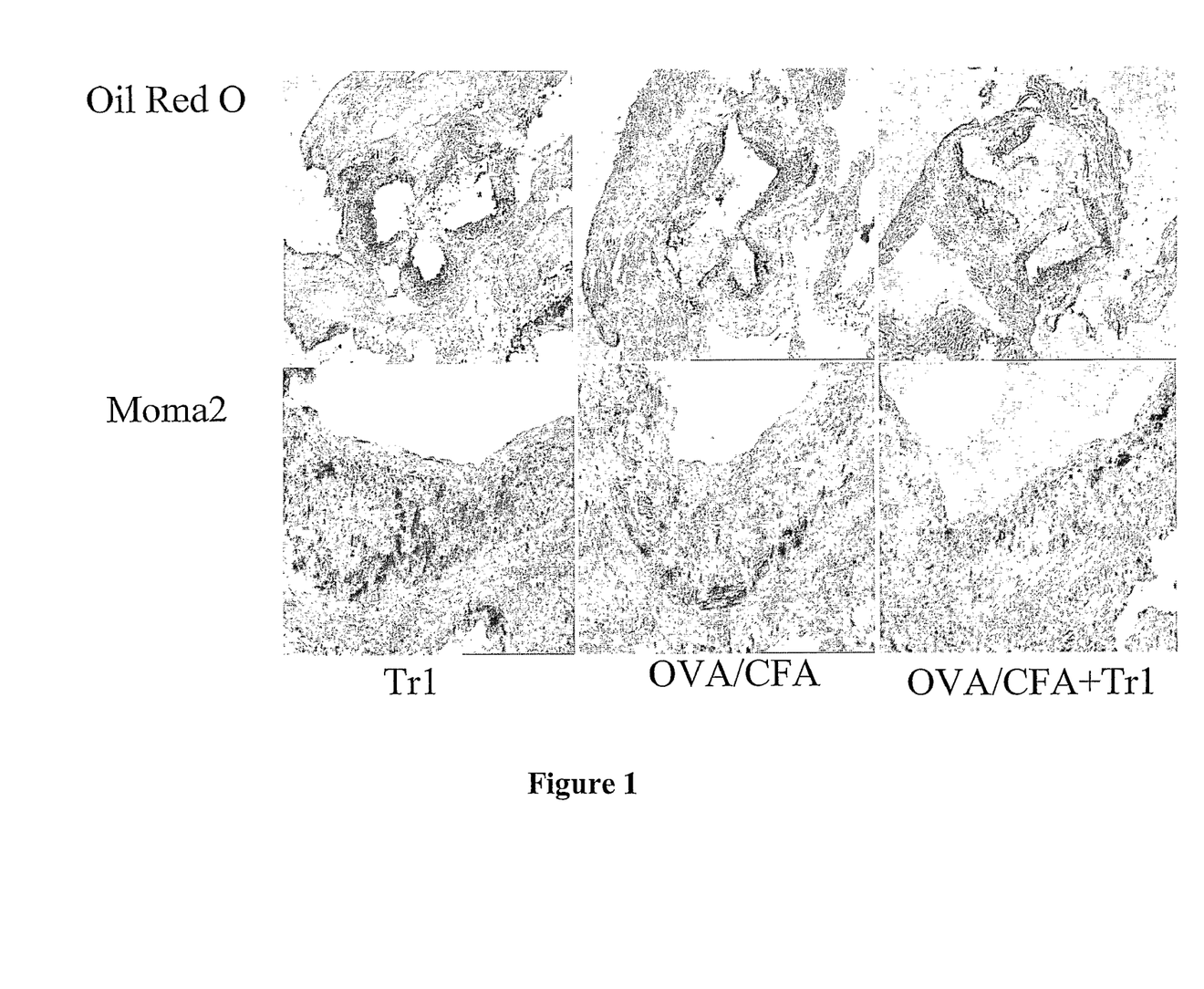
FIG. 1 depicts representative photomicrographs show sections of advanced atherosclerotic plaques (Oil red O staining) from the aortic sinus of mice treated with Tr1, OVA/CFA, or (OVA/CFA)+Tr1. There was a substantial reduction in lesion size in OVA/CFA+Tr1 group. There was also a reduction in macrophage infiltration (red MOMA-2 staining) within lesions of mice treated with OVA/CFA+Tr1 compared with either Tr1- or OVA/CFA-treated mice. Original magnifications: ×40 for Oil red O staining; ×400 for MOMA-2 staining.
Figure 2:
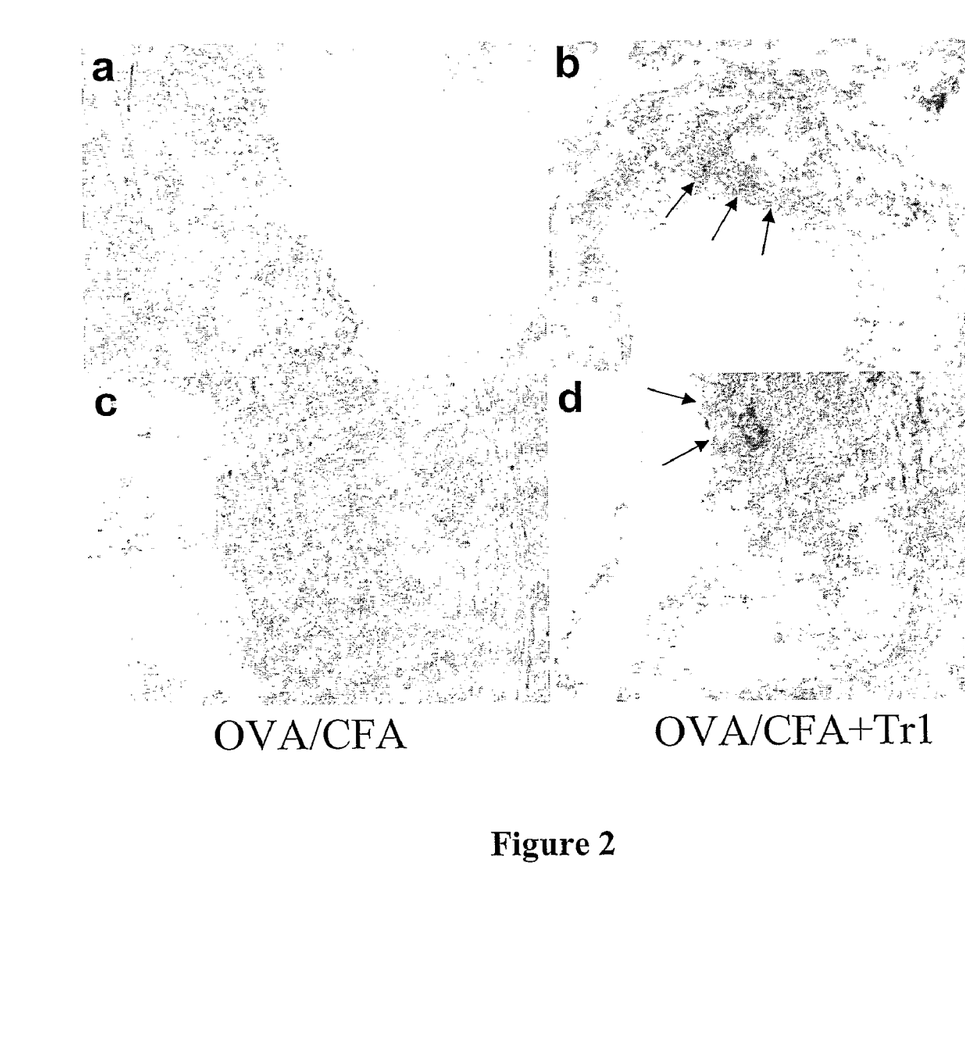
FIG. 2 depicts representative photomicrographs show IL-10 red staining (arrows) in sections of advanced atherosclerotic plaques from the aortic sinus of mice treated with OVA/CFA (a, c), or (OVA/CFA)+Tr1 (b, d). Intense IL-10 staining (arrows in b and d) was found in plaques of mice treated with OVA/CFA+Tr1. Original magnifications: a and b, ×200; c and d, ×400.

Atherosclerotic lesion size in the aortic sinus did not differ between saline, Tr1 and OVA/CFA-treated animals. However, we found a highly significant decrease of plaque size in the (OVA/CFA)+Tr1 group compared with either saline (P=0.002), Tr1 (P<0.0001) or OVA/CFA group (P=0.001) (Table 3 and FIG. 1). Despite the significant decrease in legion size, plaques of mice treated with (OVA/CFA)+Tr1 showed a marked decrease in relative macrophage infiltration (32% to 46% reduction, Table 3 and FIG. 1), and T cell accumulation (37% to 50% reduction, Table 3), with no change in smooth muscle cell or collagen content (Table 3). In addition, we found intense Il-10 staining in the plaques of mice treated with (OVA/CFA)+Tr1 whereas no or barely detectable levels of IL-10 were found in plaques from the other 3 groups (FIG. 2). IL-10 staining was also detected in the adventitia of all study groups but was clearly enhanced in (OVA/CFA)+Tr1 group (FIG. 2). Overall, these results suggest that a regulatory T cell response is associated with a less pronounced inflammatory plaque phenotype.

2.3 Discussion

A substantial body of evidence suggests an important role for Th1-mediated immuno-inflammatory responses in the development and progression of atherosclerotic lesions, at least in experimental models of human-like atherosclerosis (3 to 10). There are also reports from human studies suggesting a strong association between Th1-related responses and plaque instability (9, 26 to 29). Therefore, much of the recent research in the field of atherosclerosis, based on current dogma suggesting that the immuno-inflammatory response in atherosclerosis is controlled by distinct Th1 and Th2 subpopulations of T cells, has focused on the potential role of Th2-mediated responses in the modulation of the atherosclerotic process. The finding by several independent groups that IL-10, a Th2-related cytokine, exerts major anti-atherogenic effects, has particularly reinforced the Th1/Th2 paradigm in immunity to atherosclerosis (11, 30 to 33). However, IL-10 is not specific of Th2 cells. Interestingly, another subtype of T cells, Tr1, with cytokine profiles distinct from either Th1 or Th2 cells, has been identified and shown to play an important role in the regulation and protection against various Th1- and Th2-mediated immuno-inflammatory diseases (see 12 to 14 for review). Therefore, we hypothesized that, in atherosclerosis, there may be an imbalance between the effector and the regulatory (Tr1 for instance) arms of the immune response, and suggested that supplementation with Tr1 cells may lead to the induction of a regulatory immune phenotype and a reduction in Th1- (and Th2) mediated responses, ultimately altering plaque development and/or composition.

Here, we showed that these regulatory Tr1 cells, when transferred into mice with their cognate antigen, induced a significant suppression of Th1-mediated responses and led to an increase in IL-10 production by stimulated peripheral T cells. Tr1-mediated immune suppression was observed in response to stimulation with either OVA or ConA, suggesting the induction of a systemic bystander immune suppression, which most likely resulted from repetitive administration of OVA/CFA. Interestingly, the induction of Tr1 responses was associated with a significant reduction in atherosclerotic plaque size, a marked reduction in the relative accumulation of inflammatory macrophages and T lymphocytes with a preservation of smooth muscle cell and collagen contents. It is noteworthy that the transfer and in vivo activation of Tr1 cells led to a profound reduction in the ratio of IFN-γ to IL-10 compared with the other groups (Table 2), and to the appearance of intense IL-10 staining within the plaques, suggesting that this change in the balance between pro- and anti-atherogenic mediators may have contributed to the alterations in lesion development and composition. These results show that modulation of the immune response is achievable by transfer and activation of Tr1 cells, and leads to limitation of the development of atherosclerosis in apoE deficient mice. It could be argued that our data may simply be compatible with a systemic effect of circulating IL-10 and that such effect may be independent of any regulatory or immuno-suppressive function. Although it is very difficult to separate the regulatory functions of Tr1 clones from their capacity to produce IL-10 (several studies have established the critical contribution of the immuno-modulatory cytokine IL-10 to the regulatory potential of Tr1, reviewed in (12, 13), we believe that several data argue against such hypothesis. First, we have been unable to detect any substantial production or difference in serum IL-10 levels between the various study groups whereas IL-10 protein accumulation was increased locally within the plaques of OVA/CFA+Tr1 group. Second, not all IL-10-producing T cells are regulatory T cells. Pinderski et al (33) have recently shown that overexpression of IL-10 by T lymphocytes (IL-10 was placed under the control of the IL-2 promoter) led to a switch toward a Th2 phenotype, which is phenotypically and functionally distinct from all Tr1 clones. Unlike the results obtained with the overexpression of IL-10 in the latter study (33), the inventors have shown in their work that appropriate activation of Tr1 led to significant reductions in both Th1 (IFN-γ) and Th2-related cytokines (IL-4 and IL-5) and immunoglobulins (IgG2a and IgE, respectively) (Tables 1 and 2). This is consistent with previous studies showing that only regulatory T cells, like Tr1, are able to suppress both Th1 and Th2-related responses (12, 13, 20, 24).

Another potential limitation to our study is the confounding effect of CFA on atherosclerotic lesion development. Indeed, previously published studies have reported a reduction in atherosclerosis with CFA/IFA (34, 35). These reductions in the aortic arch or the thoracic aorta were moderate (18% and 19%) and were accompanied with changes in total and/or HDL-cholesterol levels that may have contributed to limitation of plaque progression. It is noteworthy that in our study, the OVA/CFA group showed a similar reduction in atherosclerotic lesion size in the thoracic aorta (23%) as that reported in studies using CFA/IFA, even in the absence of changes in cholesterol levels. However, in our study the additional transfer of Tr1 cells resulted in a much more important and marked 55% reduction in atherosclerosis.

In conclusion, our results provide the first proof of concept that cell transfer of a novel subpopulation of T cells with regulatory functions, here Tr1 cells, is able to modulate the in vivo immune response and leads to substantial limitation of plaque size while inducing changes in plaque composition indicative of a less inflammatory plaque phenotype. This work paves the way for the development and testing of novel therapeutic strategies based on the enhancement and/or transfer of specific regulatory immune cells (i.e., Tr1 cells specific for a plaque-derived antigen) to limit the development and prevent the complications of atherosclerosis.

TABLE 1

Proliferation and cytokine production by OVA-stimulated lymph nodes T cells, and serum levels of OVA-specific IgG2a and IgE.

|  | Saline (n = 5) | OVA/CFA (n = 9) | Tr1 (n = 6) | Tr1 + OVA/CFA (n = 9) |
|---|---|---|---|---|
| IFN-γ (ng/ml) | 0.01 ± 0.001 | 3.34 ± 1.2* | 0.02 ± 0.001 | 1.4 ± 0.2† |
| IL-10 (ng/ml) | 0.1 ± 0.02 | 0.34 ± 0.09* | 0.09 ± 0.01 | 1.3 ± 0.3† |
| IL-4 (pg/ml) | 0 | 0 | 0 | 0 |
| IL-5 (ng/ml) | 0.01 ± 0.001 | 0.16 ± 0.02* | 0 | 0.1 ± 0.01† |
| Proliferation (cpm) | 1 231 ± 136 | 25 147 ± 1 267 | 1 567 ± 637 | 9 547 ± 957† |
| IgG2a (ng/ml) | 0.677 ± 0.09 | 10,555 ± 2,254* | 0.11 ± 0.01 | 3,567 ± 985† |

TABLE 1-continued

Proliferation and cytokine production by OVA-stimulated lymph nodes T cells, and serum levels of OVA-specific IgG2a and IgE.

|  | Saline (n = 5) | OVA/CFA (n = 9) | Tr1 (n = 6) | Tr1 + OVA/CFA (n = 9) |
|---|---|---|---|---|
| IgE (pg/ml) | 0 | 57 ± 12* | 0 | 29.1 ± 9† |

*$P < 0.001$ vs saline, †$P < 0.001$ vs OVA/CFA
Results are expressed as mean ± SD.

TABLE 2

Cytokine production by conA-stimulated splenic T cells.

|  | Saline (n = 5) | OVA/CFA (n = 9) | Tr1 (n = 6) | Tr1 + OVA/CFA (n = 9) |
|---|---|---|---|---|
| IFN-γ (ng/ml) | 2.63 ± 1.6 | 3.39 ± 1.5* | 2.6 ± 1.3 | 1.7 ± 0.3† |
| IL-10 (ng/ml) | 0.5 ± 0.05 | 1.05 ± 0.2* | 0.58 ± .0.1 | 1.2 ± 0.2 |
| IL-4 (pg/ml) | 137 ± 27 | 54 ± 12 | 148 ± 31 | 0 |
| IL-5 (ng/ml) | 0.68 ± 0.03 | 0.3 ± 0.1* | 0.69 ± 0.08 | 0.12 ± 0.05† |

*$P < 0.001$ vs saline, †$P < 0.001$ vs OVA/CFA
Results represent mean ± SD.

TABLE 3

Serum cholesterol levels, atherosclerotic lesion size and composition (mean ± SEM) in the aortic sinus of apoE deficient mice.

|  | Saline (n = 5) | OVA/CFA (n = 9) | Tr1 (n = 6) | Tr1 + OVA/CFA (n = 9) |
|---|---|---|---|---|
| Total cholesterol (g/l) | 4.22 ± 0.2 | 4.03 ± 0.13 | 4.05 ± 0.19 | 3.90 ± 0.15 |
| HDL cholesterol (g/l) | 0.17 ± 0.04 | 0.11 ± 0.02 | 0.14 ± 0.02 | 0.13 ± 0.01 |
| Lesion size in thoracic aorta (%) | 8.4 ± 0.9 | 6.5 ± 0.7 | 8.5 ± 1.0 | 3.8 ± 0.3* |
| Lesion size in aortic sinus (μm$^2$) | 323 564 ± 28 956 | 317 120 ± 13 464 | 376 102 ± 22 697 | 234 511 ± 11 797† |
| MOMA2-positive area (%) | 34.6 ± 1.8 | 27.3 ± 2.3 | 31.4 ± 3.6 | 18.6 ± 1.4‡ |
| CD3-positive (cells/mm$^2$) | 283.5 ± 31.7 | 314.5 ± 39.6 | 257.2 ± 29.4 | 159.2 ± 25.3§ |
| α-actine positive area (%) | 5.0 ± 1.1 | 4.9 ± 0.9 | 5.8 ± 1.0 | 4.6 ± 0.9 |
| Sirius red-positive area (%) | 37.5 ± 2.4 | 39.6 ± 2.3 | 39.6 ± 3.9 | 35.4 ± 2.2 |

*$P = 0.0002$ vs Tr1; $P = 0.008$ vs OVA/CFA and $P = 0.0003$ vs saline.
†$P < 0.0001$ vs Tr1; $P = 0.001$ vs OVA/CFA and $P = 0.002$ vs saline.
‡$P = 0.0006$ vs Tr1; $P = 0.006$ vs OVA/CFA and $P < 0.0001$ vs saline.
§$P < 0.05$ vs Tr1; $P = 0.001$ vs OVA/CFA and $P = 0.02$ vs saline.

REFERENCES

1. Lusis A J. Atherosclerosis. *Nature.* 2000; 407:233-41.
2. Glass C K, Witztum J L. Atherosclerosis. the road ahead. *Cell.* 2001; 104:503-16.
3. Hansson G K. Immune mechanisms in atherosclerosis. *Arterioscler Thromb Vasc Biol.* 2001; 21:1876-90.
4. Gupta S, Pablo A M, Jiang X C, et al. IFN-gamma potentiates atherosclerosis in apoE knock-out mice. *J Clin Invest.* 1997; 99:2752-2761.
5. Whitman S C, Ravisankar P, Elam H, et al. Exogenous interferon-gamma enhances atherosclerosis in apolipoprotein E−/− mice. *Am J Pathol.* 2000; 157:1819-24.
6. Lee T S, Yen H C, Pan C C, et al. The role of interleukin 12 in the development of atherosclerosis in ApoE-deficient mice. *Arterioscler Thromb Vasc Biol.* 1999; 19:734-42.
7. Zhou X, Nicoletti A, Elhage R, et al. Transfer of CD4(+) T cells aggravates atherosclerosis in immunodeficient apolipoprotein E knockout mice. *Circulation.* 2000; 102:2919-22.
8. Laurat E, Poirier B, Tupin E, et al. In vivo downregulation of T helper cell 1 immune responses reduces atherogenesis in apolipoprotein E-knockout mice. *Circulation.* 2001; 104:197-202.
9. Mallat Z, Corbaz A, Scoazec A, et al. Interleukin-18/interleukin-18 binding protein signaling modulates atherosclerotic lesion development and stability. *Circ Res.* 2001; 89:E41-5.
10. Whitman S C, Ravisankar P, Daugherty A. Interleukin-18 enhances atherosclerosis in apolipoprotein E(−/−) mice through release of interferon-gamma. *Circ Res.* 2002; 90:E34-8.
11. Daugherty A, Rateri D L. T lymphocytes in atherosclerosis: the yin-yang of Th1 and Th2 influence on lesion formation. *Circ Res.* 2002; 90:1039-40.
12. Groux H. An overview of regulatory T cells. *Microbes Infect.* 2001; 3:883-9.
13. Roncarolo M G, Bacchetta R, Bordignon C, et al. Type 1 T regulatory cells. *Immunol Rev.* 2001; 182:68-79.

14. McGuirk P, Mills K H. Pathogen-specific regulatory T cells provoke a shift in the Th1/Th2 paradigm in immunity to infectious diseases. *Trends Immunol.* 2002; 23:450-5.

15. Groux H, Bigler M, O'Garra A, et al. A CD4+ T-cell subset inhibits antigen-specific T cell responses and prevents colitis. *Nature.* 1997; 389:737-742.

16. Doetze A, Satoguina J, Burchard G, et al. Antigen-specific cellular hyporesponsiveness in a chronic human helminth infection is mediated by T(h)3/T(r)1-type cytokines IL-10 and transforming growth factor-beta but not by a T(h)1 to T(h)2 shift. *Int Immunol.* 2000; 12:623-30.

17. Cavani A, Nasorri F, Prezzi C, et al. Human CD4+ T lymphocytes with remarkable regulatory functions on dendritic cells and nickel-specific Th1 immune responses. *J Invest Dermatol.* 2000; 114:295-302.

18. Levings M K, Sangregorio R, Galbiati F, et al. IFN-alpha and IL-10 induce the differentiation of human type 1 T regulatory cells. *J Immunol.* 2001; 166:5530-9.

19. MacDonald A J, Duffy M, Brady M T, et al. CD4 T helper type 1 and regulatory T cells induced against the same epitopes on the core protein in hepatitis C virus-infected persons. *J Infect Dis.* 2002; 185:720-7.

20. McGuirk P, McCann C, Mills K H. Pathogen-specific T regulatory 1 cells induced in the respiratory tract by a bacterial molecule that stimulates interleukin 10 production by dendritic cells: a novel strategy for evasion of protective T helper type 1 responses by *Bordetella pertussis*. *J Exp Med.* 2002; 195:221-31.

21. Fukaura H, Kent S C, Pietrusewicz M J, et al. Induction of circulating myelin basic protein and proteolipid protein-specific transforming growth factor-beta1-secreting Th3 T cells by oral administration of myelin in multiple sclerosis patients. *J Clin Invest.* 1996; 98:70-7.

22. Chen Y, Kuchroo V K, Inobe J, et al. Regulatory T cell clones induced by oral tolerance: suppression of autoimmune encephalomyelitis. *Science.* 1994; 265:1237-40.

23. Shevach E M. Regulatory T cells in autoimmunity*. *Annu Rev Immunol.* 2000; 18:423-49.

24. Cottrez F, Hurst S D, Coffman R L, et al. T regulatory cells 1 inhibit a Th2-specific response in vivo. *J Immunol.* 2000; 165:4848-53.

25. Barrat F J, Cua D J, Boonstra A, et al. In vitro generation of interleukin 10-producing regulatory CD4(+) T cells is induced by immunosuppressive drugs and inhibited by T helper type 1 (Th1)- and Th2-inducing cytokines. *J Exp Med.* 2002; 195:603-16.

26. Liuzzo G, Kopecky S L, Frye R L, et al. Perturbation of the T-cell repertoire in patients with unstable angina [see comments]. *Circulation.* 1999; 100:2135-9.

27. Liuzzo G, Goronzy J J, Yang H, et al. Monoclonal T-cell proliferation and plaque instability in acute coronary syndromes. *Circulation.* 2000; 101:2883-8.

28. Liuzzo G, Vallejo A N, Kopecky S L, et al. Molecular fingerprint of interferon-gamma signaling in unstable angina. *Circulation.* 2001; 103:1509-14.

29. Mallat Z, Henry P, Fressonnet R, et al. Increased plasma concentrations of interleukin-18 in acute coronary syndromes. *Heart.* 2002; 88:467-9.

30. Mallat Z, Besnard S, Duriez M, et al. Protective role of interleukin-10 in atherosclerosis. *Circ Res.* 1999; 85:e17-24.

31. Pinderski Oslund L J, Hedrick C C, Olvera T, et al. Interleukin-10 blocks atherosclerotic events In vitro and In vivo. *Arterioscler Thromb Vasc Biol.* 1999; 19:2847-53.

32. Von Der Thusen J H, Kuiper J, Fekkes M L, et al. Attenuation of atherogenesis by systemic and local adenovirus-mediated gene transfer of interleukin-10 in LDLr−/− mice. *Faseb J.* 2001; 15:2730-2.

33. Pinderski L J, Fischbein M P, Subbanagounder G, et al. Overexpression of interleukin-10 by activated T lymphocytes inhibits atherosclerosis in LDL receptor-deficient Mice by altering lymphocyte and macrophage phenotypes. *Circ Res.* 2002; 90:1064-71.

34. Hansen P R, Chew M, Zhou J, et al. Freunds adjuvant alone is antiatherogenic in apoE-deficient mice and specific immunization against TNFalpha confers no additional benefit. *Atherosclerosis.* 2001; 158:87-94.

35. Binder C J, Horkko S, Dewan A, et al. Pneumococcal vaccination decreases atherosclerotic lesion formation: molecular mimicry between *Streptococcus pneumoniae* and oxidized LDL. *Nat Med.* 2003; 9:736-43.

The invention claimed is:

1. A method of treating or limiting the development of atherosclerosis comprising administering sequentially, simultaneously or separately to a mammal in need of such a treatment:
   a) a Tr1 cell population obtained from a CD4+ T lymphocyte population of the mammal, wherein the Tr1 cell population has been activated in vitro in the presence of an antigen, wherein the antigen is selected from the group consisting of a non-allergic food antigen and a non-pathogenic bacterial antigen, and
   b) the antigen which has been used to activate the Tr1 cell population, wherein the antigen is administered via a subcutaneous route.

2. The method of claim 1, wherein said antigen is an immunogenic peptide or protein.

3. The method of claim 1, wherein between 0.05 mg/kg to 5 mg/kg of said antigen is administered to said mammal.

4. The method of claim 1, wherein the antigen is administered to the mammal once or twice the first month and then once a month for about the next 2 to 3 months.

5. The method of claim 1, wherein from $10^6$ to $10^9$ antigen-activated Tr1 cells/kg are administered to the mammal.

6. The method of claim 1, comprising intravenous, intramuscular, intra-arterial, intramedullary, intrathecal, intraventricular, transdermal, or subcutaneous administration of said antigen-activated Tr1 cells.

7. The method of claim 1, wherein the antigen-activated Tr1 cell population is obtained by an in vitro preparation process comprising the following steps:
   i) obtaining a Tr1 cell population from the CD4+ T lymphocyte population of the mammal in need of the treatment;
   ii) in vitro activating the Tr1 cell population by contacting it with the antigen of step b); and
   iii) recovering the antigen-activated Tr1 cell population.

8. The method of claim 7, wherein the step i) of obtaining the Tr1 cell population comprises the following steps:
   a) isolating a progenitor cell population from said mammal;
   b) obtaining a population of dendritic cells by culturing said progenitor cell population in presence of interleukine-10 (IL-10);
   c) contacting cells of step b) with the CD4+ T lymphocyte population isolated from said mammal to allow differentiation of said CD4+ T lymphocytes into the Tr1 cell population; and d) recovering the Tr1 cell population from the step c).

9. The method of claim 7, wherein the step i) of obtaining the Tr1 cell population comprises the following steps:
   a) contacting the CD4+ T lymphocyte population with an appropriate amount of alpha-interferon (α-IFN); and
   b) recovering the Tr1 cell population.

10. The method of claim 9, wherein the step a) of contacting is in combination with an appropriate amount of IL-10, such as 100 Uml$^{-1}$.

11. The method of claim 9, wherein the Tr1 cell population is further proliferated in interleukine 15 (IL-15).

12. The method of claim 1, wherein the antigen-activated Tr1 cell population is obtained by an in vitro preparation process comprising the following steps:
   i) obtaining a CD4+ T lymphocyte population from the mammal in need of the treatment and in vitro activating the CD4+ T lymphocyte population in the presence of the antigen of step b), wherein the antigen is presented by artificial antigen presenting cells;
   ii) recovering an activated CD4+ T lymphocyte population comprising at least 10% of the antigen-activated Tr1 cell population; and
   iii) recovering the antigen-activated Tr1 cell population.

13. The method of claim 12, wherein the artificial antigen presenting cells express a HLA II system molecule and a human LFA-3 molecule, and do not express the co-stimulation molecules B7-1, B7-2, B7-H1, CD40, CD23 and ICAM-I.

14. The method of claim 1, wherein the antigen-activated Tr1 cell population is obtained by an in vitro preparation process comprising the following steps:
   i) obtaining a CD4+ T lymphocyte population from the mammal in need of the treatment and in vitro activating the CD4+ T lymphocyte population in the presence of the antigen of step b) and an appropriate amount of interleukine-10 (IL-10); and
   ii) recovering the antigen-activated Tr1 cell population.

15. The method of claim 1, wherein the mammal in need of such a treatment is a human being.

16. The method of claim 1, wherein Tr1 cells are purified with flow cytometry or immunoaffinity using at least one of the following antibodies:
   anti-CD4,
   anti-CD3,
   anti-CD18, and
   anti-CD49b.

17. The method of claim 16, wherein prior to purification of the Tr1 cells, enrichment of CD3+CD4+CD18brightCD49b+ cells from lymphocytes is obtained by the following steps:
   depleting the total T lymphocyte population with anti-human Ig-magnetic beads of cells bound with human anti-CD8, anti-CD14, anti-CD56 and anti-CD19,
   selecting CD49b+ cells bound to an anti-CD49b human antibody with anti-human Ig-magnetic beads.

* * * * *